United States Patent [19]

Knopp et al.

[11] Patent Number: 4,623,795

[45] Date of Patent: Nov. 18, 1986

[54] IRRADIATING DEVICE

[75] Inventors: Arthur A. Knopp, Chalfont; Nathaniel H. Lieb, Narberth; Albert D. Alderman, Jr., Skippack, all of Pa.

[73] Assignee: Penn-Med Technology, Inc., West Conshohocken, Pa.

[21] Appl. No.: 613,860

[22] Filed: May 24, 1984

[51] Int. Cl.[4] ............................................. F21V 29/00
[52] U.S. Cl. ............................ 250/504 H; 250/493.1
[58] Field of Search ............ 250/504 H, 504 R, 493.1

[56] References Cited

U.S. PATENT DOCUMENTS

| D. 280,929 | 10/1985 | Lystager | D24/10 |
|---|---|---|---|
| 3,792,230 | 2/1974 | Ray | 250/504 |
| 3,811,044 | 5/1974 | Meador | 250/504 |
| 4,149,086 | 4/1979 | Nath | 250/504 |

*Primary Examiner*—Bruce C. Anderson
*Assistant Examiner*—Jack I. Berman
*Attorney, Agent, or Firm*—Caesar, Rivise, Bernstein & Cohen

[57] ABSTRACT

An irradiation device for directing radiation onto a substance in a desired wavelength range for curing the substance, and particularly for use in curing substances on the teeth of dental patients. A light-emitting lamp assembly is located within a plastic housing of the device, and a heat shield surrounds the lamp assembly to divide the housing into an outer chamber between the shield and housing, and an inner chamber within the shield. The housing includes an entrance conduit for receiving pressurized cooling air, and a channeling arrangement is provided for directing the pressurized cooling air from the entrance conduit, through the outer and inner chambers within the housing, and out of the housing through exit passages.

15 Claims, 7 Drawing Figures

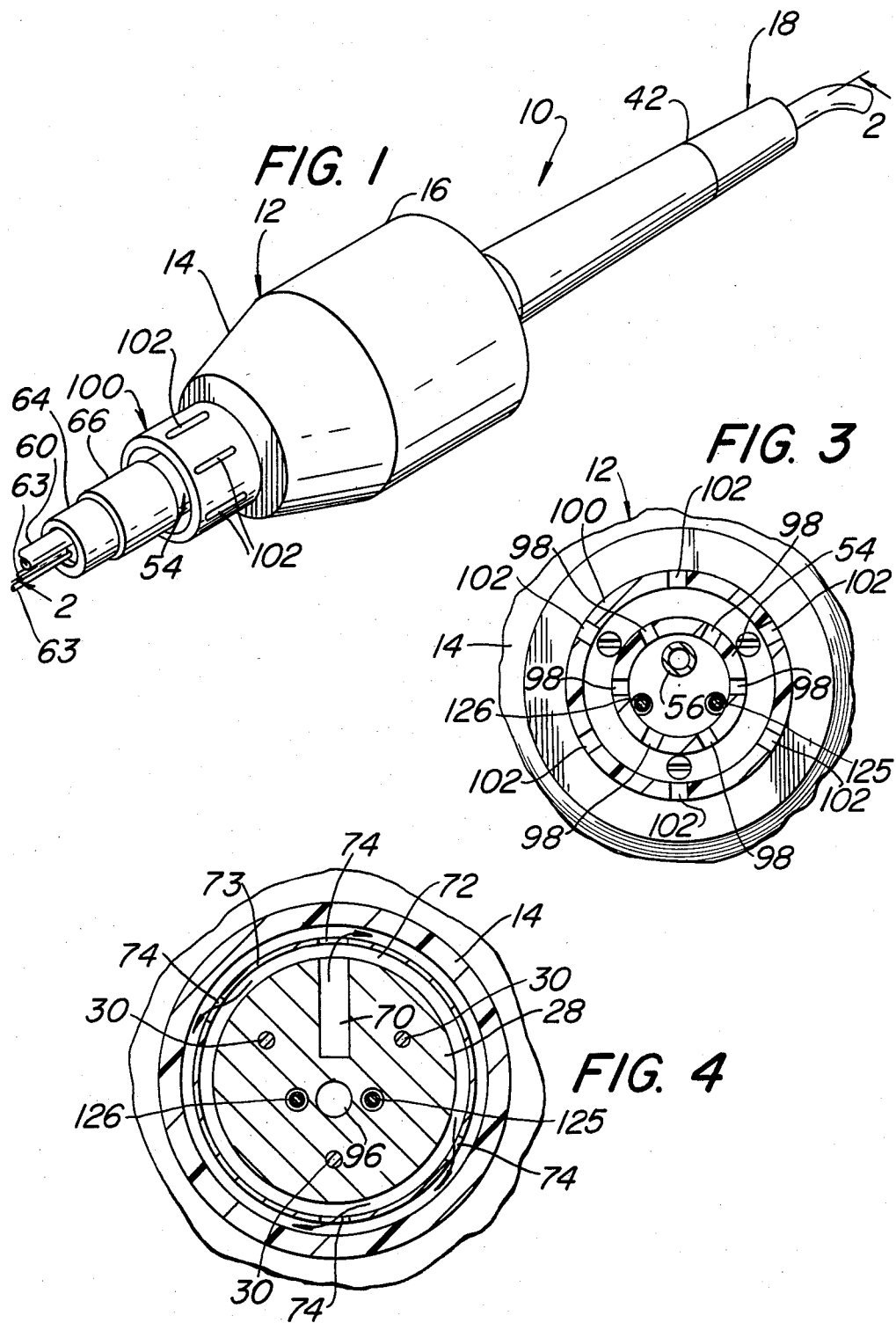

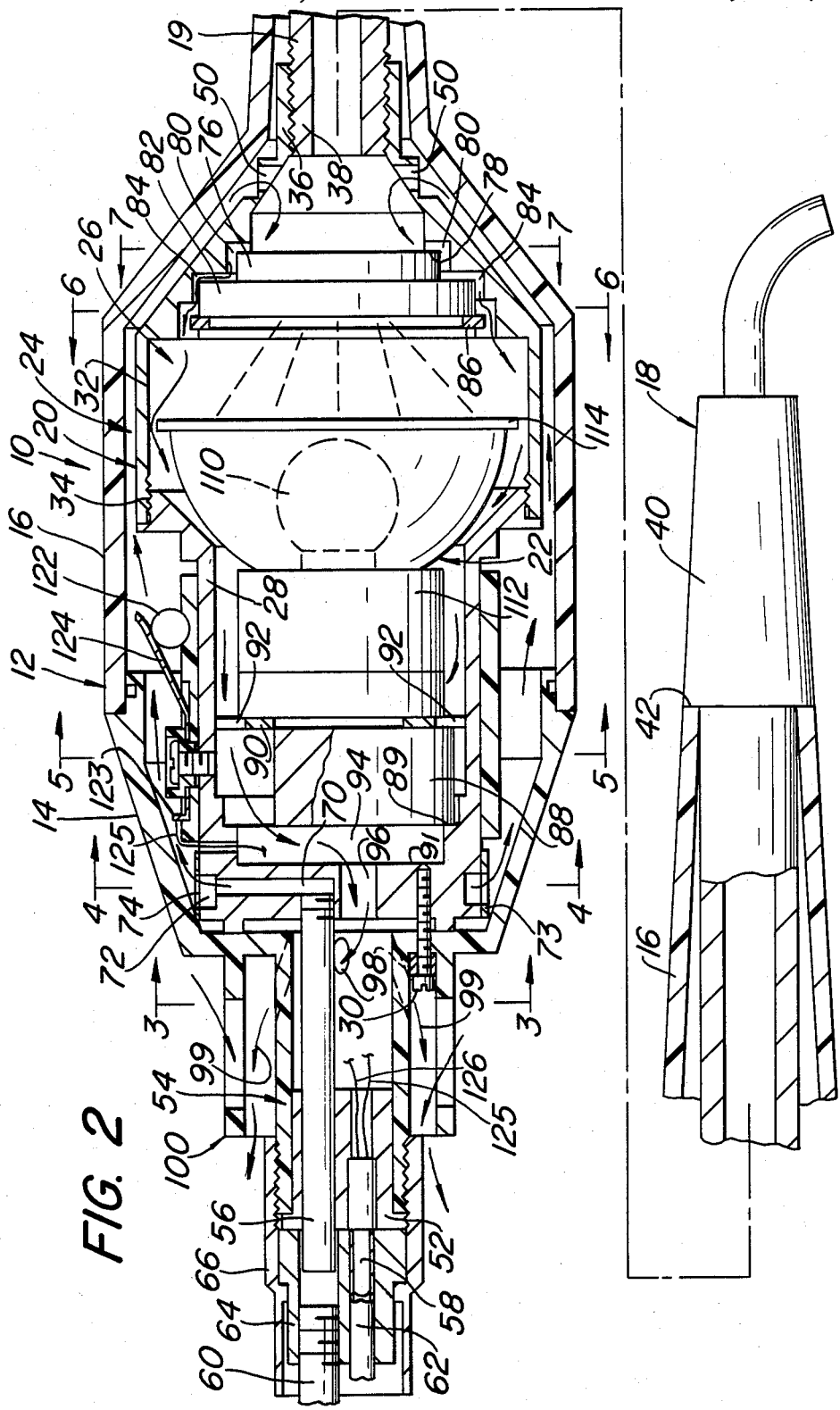

IRRADIATING DEVICE

BACKGROUND OF THE INVENTION

This invention relates generally to an irradiating device, and more specifically to a device for emitting radiation in a wavelength range for curing a substance.

Devices for irradiating substances curable by radiation in a selected spectral range are known in the prior art. For example, such devices are utilized in the dental field to cure coatings on teeth of patients for, among other purposes, protecting against caries.

In U.S. Pat. No. 3,712,984, issued to Lienhard, a device is disclosed for emitting radiation in the UVA range in excess of 320 nanometers for curing an adhesive sealant on teeth of a patient. The disclosed device includes a handle projecting generally normal to a body section in which the light generating source is housed. A separate base is provided to support this device, and a blower or fan is provided in the base to cool the device while it is out-of-service. A fan or blower is not provided to cool the device while it is in service.

U.S. Pat. No. 3,970,856, issued to Mahaffey et al., discloses a linearly oriented, hand-held applicator for generating light in the ultraviolet range for use in dental applications. This applicator does not employ a fan or blower system to cool it.

U.S. Pat. No. 4,298,806, issued to Herold, discloses a device for selectively reflecting radiation in the UVA range (320-400 nanometer) and near -UVA range (400-500 nanometer) by the use of a reflector system partially surrounding a commercially available tungsten filament lamp. The reflected radiation is directed through a waveguide to an outlet adapted to be positioned adjacent a tooth to be treated. The device includes a handle extending at an angle from the main body in which the light source is housed, and a fan is included in the handle to provide a cooling air flow. In operation the fan pulls air into the main housing from both the rear and front sides thereof and directs the air through the base of the handle. While the use of a fan, as disclosed in the Herold device, may provide adequate cooling for short periods of use, a more optimum cooling system is believed to be desirable for these types of curing devices.

U.S. Pat. No. 4,149,086, issued to Nath, discloses an irradiation device for directing radiation in the UVA range of 300-420 nanometer through a light guide for use in dental applications. Nath specifically illustrates the use of a fan located in a handle section of the device to establish the desired cooling effect. By way of general discussion Nath states that the fan could be replaced with a connection to a pressurized gas source for producing a desired cooling air flow. However, there is no disclosure as to how the pressurized gas would be connected to the device, or the manner in which the air flow would be channeled through the device.

Although a number of different irradiating devices utilizable in the dental field are disclosed in the prior art, a need still is believed to exist for a compact, easy-to-manipulate unit provided with improved air flow characteristics to prevent overheating in a manner superior to that achieved in prior art devices.

OBJECTS OF THE INVENTION

It is a general object of this invention to provide an irradiating device which is compact and easy to handle.

It is a further object of this invention to provide an irradiating device which is cooled in an effective manner during use.

It is a more specific object of this invention to provide an irradiating device for use in curing substances applied to the teeth of dental patients which is easy to handle and efficiently cooled during use.

SUMMARY OF THE INVENTION

The above and other objects of this invention are achieved in an irradiation device for directing radiation onto a substance in a desired wavelength range for curing said substance. The device includes an elongate housing with a light transmitting tip extending outwardly of the forward end thereof. A downstream end of the tip is adapted to be positioned adjacent the substance to be irradiated, and an upstream end of the tip is positioned to receive radiation emitted from a light-emitting lamp assembly in the housing. A heat shield is located inwardly of the outer wall of the elongate housing, surrounds the light-emitting lamp assembly and bridges the space between the lamp assembly and the upstream end of the light transmitting tip to define an outer chamber between the shield and outer wall of the housing and an inner chamber within the shield. Both of the inner and outer chambers receive a circulating flow of cooling air. An entrance conduit for receiving pressurized air communicates through the rear end of the housing for attachment to a source of pressurized gas, and channelling means are associated with the conduit for directing pressurized air from the conduit, through the outer and inner chambers, and then out of the housing through an exit conduit.

Other objects and many of the attendant advantages of this invention will be readily appreciated as the same becomes better understood by reference to the following detailed description when considered in connection with the accompanying drawings.

BRIEF DESCRIPTION OF THE DRAWINGS

FIG. 1 is an isometric view of an irradiating device in accordance with this invention;

FIG. 2 is an enlarged sectional view taken along line 2—2 of FIG. 1;

FIG. 3 is a sectional view taken along line 3—3 of FIG. 2;

FIG. 4 is a sectional view taken along line 4—4 of FIG. 2;

DESCRIPTION OF THE PREFERRED EMBODIMENT OF THE INVENTION

Figure 5:
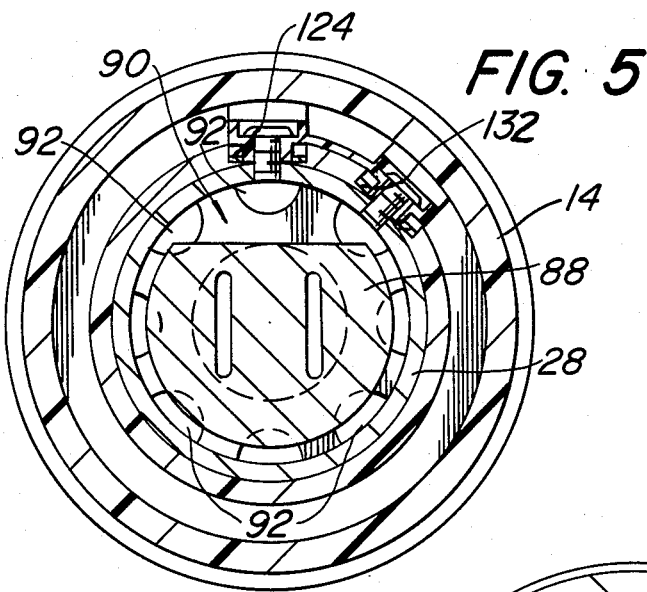
FIG. 5 is a sectional view taken along line 5—5 of FIG. 2.

Referring now in greater detail to the various figures of the drawings wherein like reference characters refer to like parts, an irradiating device embodying the present invention is generally shown at 10 in FIG. 1. The device 10 basically includes an elongate plastic housing 12 in which a lamp assembly 22 (FIG. 2) is mounted for emitting radiation having a component in a wavelength range for curing a substance. That component is transmitted through a light transmitting tip 18 of the device for curing the substance.

In the preferred embodiment of the invention the irradiating device 10 is utilized in the dental field for directing radiation in the visible blue range, preferably about 460 nanometers, through the light transmitting tip 18 to cure an adhesive substance on teeth of dental patients. The tip 18 includes a fiber optic bundle within an outer metal sleeve 19; however other light transmitting elements can be used, if desired.

Referring to FIGS. 1 and 2, the elongate housing 12 includes a rear molded section 14 and a front molded section 16. These sections are retained in proper position relative to each other in a unique manner by the light transmitting tip 18, in a manner to be described hereinafter. As can be seen best in FIG. 2 a heat shield 20 encloses the lamp assembly 22 within the interior of the plastic housing 12. The lamp assembly 22 preferably is of a conventional type employed in movie or slide projectors for emitting and reflecting radiation in the visible range (i.e., approximately 350 nm–750 nm). The heat shield 20 is spaced radially inward from the outer wall of the elongate housing 12 to divide the internal compartment of the housing into an outer annular chamber 24 between the shield and housing, and an inner cylindrical chamber 26 within the shield. In accordance with a unique sheet of this invention a flow of pressurized cooling air is directed through both the outer annular chamber 24 and the inner cylindrical chamber 26 to provide the desired cooling of the irradiation device.

Referring to FIGS. 2 and 3, the heat shield 20 includes a rear section 28 affixed to the plastic housing 12 by a plurality of circumferentially spaced-apart screws 30. The shield further includes a forward section 32 secured to the rear section 28 through a suitable threaded connection 34. This forward section overlies the lamp assembly 22 and bridges the region between the lamp assembly and the upstream end of the light transmitting tip 18.

As can be seen best in FIG. 2, the forward section 32 of the shield includes a threaded downstream end 36 receiving a threaded upstream end 38 of the light transmitting tip 18. The tip 18 also includes an enlarged, frustro-conical section 40 which presses against the downstream edge 42 of the front section 16 of the housing 12 to positively retain the front and rear housing sections together. The threaded connection betweem the tip and shield is between metal parts (i.e., metal forward section 32 of the heat shield 20 and outer metal sleeve 19 of the light transmitting tip 18). Thus, a threaded connection between the plastic sections of the housing is not relied upon to retain the housing sections together.

Providing the threaded connection between metal members, as opposed to plastic members, provides a more rugged and reliable system. The reason for this is that the interconnecting threads between metal members are less susceptible to becoming worn or stripped than the interconnecting threads between plastic members, when such members are repeatedly connected and separated, as is necessary to repair or replace elements in the device 10.

Referring specifically to FIG. 2, the flow of pressurized air in accordance with the preferred embodiment of this invention is in a downstream direction through the annular chamber 24, than through radially-directed passages 50 at the downstream end of the forward shield section 32, and finally in an upstream direction through the internal cylindrical chamber 26. Applicants have found that the most effective cooling is achieved by first directing the pressurized cooling air flow in a downstream direction through the outer annular chamber 24, as opposed to first directing it through the inner cylindrical chamber 26. Specifically, it has been found that directing the coolest pressurized air flow between the housing 12 and shield 20 provides the most efficient system for preventing overheating of the housing 12.

Still referring to FIG. 2, a plastic plug 52 is retained within an interior opening of rearwardly extending coupler section 54. This coupler section 54 constitutes an integrally molded part of the rear housing section 14. A conduit 56, for receiving pressurized cooling air to be directed through the device 10, and a pair of electrical male plug connectors (only one being shown at 58) for use in providing power to the lamp assembly 22, are retained within the plug 52.

Referring to FIGS. 1 and 2, an elongate conduit 60, connected to a source of pressurized gas (not shown), and a pair of female connectors (only one being shown at 62), connected to a suitable power supply (not shown) through a pair of leads 63, are retained within a plug member 64 disposed within a threaded outer connector 66. As can be seen best in FIG. 2, the threaded outer connector 66 is adapted to be threadedly received on the upstream end of the coupler section 54, with the conduit 60 aligned with the conduit 56, and the female connectors 62 receiving the male plug connectors 58.

Referring to FIGS. 2 and 4 the pressurized cooling air directed through the conduit 60 passes through the conduit 56 and into a radially extending passage 70 located in the upstream end of the rear shield section 28. The radial passage 70 communicates with an annular plenum chamber 72 provided with a closure 73. The closure 73 includes circumferentially spaced-apart openings 74 that communicate the plenum chamber 72 with the outer annular chamber 24. Thus, pressurized air directed through the conduit 60 is distributed circumferentially about the outer annular chamber 24 adjacent the upstream end thereof.

The pressurized gas, preferably air, then is forced in a downstream direction through the chamber 24, as indicated by the arrows in FIG. 2, to the downstream end of the heat shield 20. The pressurized air then passes into the inner cylindrical chamber 26 through the spaced-apart radial passages 50. The passages 50 are located between the upstream end of the light transmitting tip 18 and a blue filter 76 supported on a ledge 78 of the rear shield section 28. The blue filter is adapted to pass radiation in the blue range, on the order of approximately 460 nanometer, for subsequent passage through the light transmitting rod 18 to the substance to be cured.

Figure 7:
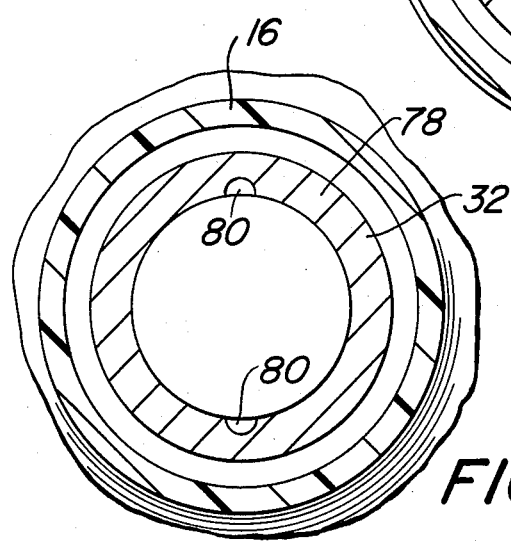
FIG. 7 is a sectional view taken along line 7—7 of FIG. 2.

As is shown in FIGS. 2 and 7, the ledge 78 is provided with undercut, or relief areas 80 diametrically opposed to each other to provide passageways through which the pressurized cooling air can flow to cool the filter 76.

Figure 6:
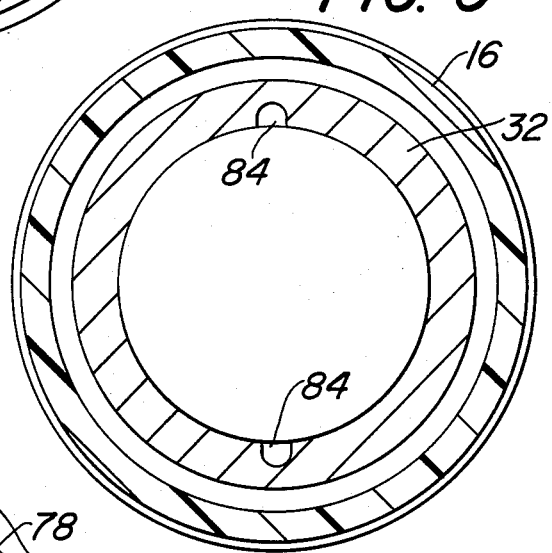
FIG. 6 is a sectional view taken along line 6—6 of FIG. 2.

Referring specifically to FIGS. 2 and 6, a heat absorbing glass filter 82 is supported on the upstream surface of the blue filter 76, and diametrically opposed relief areas 84 are provided in the forward shield section 32 to permit the flow of pressurized cooling air around the heat absorbing filter. A spring clip 86 of a conventional design is employed to retain the filters 76 and 82 in proper position within the forward heat shield section 32.

As a result of the arrangement of relief grooves adjacent the filters 76 and 82 a pressurized flow of cooling air can pass in an upstream direction over the filters and lamp assembly 22 to effectively cool them.

Referring to FIGS. 2 and 5, the lamp assembly 22 is plugged into a socket 88. The socket 88 is positioned against a forwardly facing annular ledge 89 of the heat shield 20 and the socket is retained in proper position by a spring clip 90. As can be seen best in FIG. 5, the spring clip is provided with a plurality of circumferentially spaced, semi-circular passages 92 about the periphery thereof to provide openings through which the pressurized air can flow. The annular ledge 89 spaces the rear wall of the socket from the inner back surface 91 of the rear shield section 28 to define a rear plenum chamber 94 for receiving pressurized air passing through the passages 92 in the spring clip 90.

Referring specifically to FIGS. 2 and 3, an axially directed passage 96 extends through the rear wall of the rear shield section 28 to communicate the rear plenum chamber 94 with a plurality of circumferentially spaced-apart, rearwardly inclined passages 98 extending through the peripheral wall of the coupler section 54. The rearward inclination of the passages 98 funnels the flow of pressurized air in a generally axially rearward direction, as is indicated by arrows 99. It should be noted that the air directed through the passages 98 is quite hot (i.e., approximately 250° F.), having picked up a substantial amount of heat as a result of its passage through the outer annular chamber 24 and the inner cylindrical chamber 26 of the housing 12. If this heated air were permitted to exit out the rear of the device, without first being cooled, it could provide an extremely uncomfortable environment for the dentist.

Referring to FIGS. 1–3, a further unique feature of this invention resides in the manner of mixing ambient air with the hot air directed through the passages 98 in an automatic fashion to substantially lower the temperature of the air directed rearwardly out of the device 10. To accomplish this result an outer sleeve 100 is integrally molded as part of the rear section 14 of the housing 12, and this sleeve is concentrically disposed about the coupler section 54. This outer sleeve is provided with a plurality of circumferentially spaced, axially elongate openings 102, as can be seen best in FIG. 1. As can be seen best in FIG. 3 these openings 102 are circumferentially offset (i.e., radially out of alignment) from the rearwardly inclined passages 98 extending through the wall of the coupler section 54. By staggering the arrangement of the circumferentially spaced-apart openings 102 relative to the circumferentially spaced-apart openings 98 the hot air exiting through the passages 98 will not be directed through the openings in the sleeve 102 to possibly injure the dentist. Instead, the pressurized air directed through the passages 98 will be forced to flow in a generally axial direction to create a low pressure area between the inner cylindrical coupler section 54 and the outer sleeve 100. This provides a venturi effect that sucks ambient air through the elongate openings 102 to mix with, and cool the pressurized air exiting through the passages 98. In actual operation the air exiting the passages 98 is at a temperature of approximately 250° F., and after mixing with the ambient air sucked through the openings 102, is reduced to a temperature of approximately 140° F.

The controlled movement of pressurized cooling air through the irradiation device 10, as described herein, provides a significant benefit in the present invention.

As indicated before the lamp assembly 22 can be a conventional unit of the type employed in movie and slide projectors. This lamp assembly preferably includes a conventional incandescent lamp 110 plugged into a base 112 and surrounded by an aluminum-coated, reflecting shield 114. The shield 114 directs the radiation to a focus adjacent the entrance end of the light transmitting tip 18, as is known in the art.

Referring to FIGS. 2 and 5, the electrical connection to the device 10 is made through a thermal fuse 122 by connecting one of the power leads 125 to rear end 123 of a conductive retaining clip 124 that electrically communicates with the fuse. The return connection is through a second conductive fuse-retaining clip 132 (FIG. 5), which is the same as clip 124 but is circumferentially spaced therefrom, and through the other power lead 126. Thus, in accordance with the preferred embodiment of this invention, the irradiation device is fused to prevent an overload of the system.

Without further elaboration the foregoing will so fully illustrate my invention that others may, by applying current or future knowledge, adopt the same for use under various conditions of service.

We claim:

1. A hand-held irradiation device for directing radiation onto a substance in a desired wavelength range for curing said substance, said device being characterized by an elongate housing having a rear end and a forward end; a light-emitting lamp assembly located within said housing; a light transmitting tip extending outwardly of the forward end of the housing and having a downstream end adapted to be positioned adjacent the substance to be irradiated and an upstream end for receiving radiation from the light-emitting lamp assembly; a heat shield surrounding said lamp assembly and bridging the space between said lamp assembly and the upstream end of said light transmitting tip, said shield being spaced inwardly from the outer wall of the elongate housing to define an outer chamber between the shield and housing and an inner chamber within the shield; an entrance conduit for receiving a pressurized cooling gas communicating through the rear end of the housing and being attachable to a source of pressurized gas; an exit conduit means for directing the pressurized gas out of the housing after it has moved through the outer and inner chambers and channeling means including passage means for interconnecting the entrance conduit with the outer chamber and the outer chamber with the inner chamber for directing the pressurized gas sequentially through the outer chamber, the inner chamber and then through the exit conduit means.

2. The irradiation device of claim 1 characterized in that the passage means communicating the entrance conduit with the outer chamber includes circumferentially spaced-apart openings for communicating with the outer chamber in circumferentially spaced-apart locations.

3. The irradiation device of claim 1 characterized by filter means located adjacent the upstream end of the light transmitting tip and within said shield, said channeling means directing pressurized gas over said filter means as said pressurized gas is circulated through the housing.

4. The irradiation device of claim 1 characterized in that said shield includes a rearwardly facing annular surface between the light-emitting lamp assembly and the upstream end of the light transmitting tip for supporting a filter thereon, wherein said channeling means includes passage means through a wall of said shield for communicating the outer chamber with the inner chamber in a location between the filter supported on the annular surface and the upstream end of the light transmitting tip.

5. The irradiation device of claim 1 characterized in that the exit conduit means communicates with the rear end of the housing.

6. The irradiation device of claim 5 characterized by filter means located adjacent the upstream end of the light transmitting tip and within said shield, said channeling means directing pressurized gas over said filter means as said pressurized gas is circulated through the housing.

7. The irradiation device of claim 6 characterized in that said shield includes a rearwardly facing annular surface between the light-emitting lamp assembly and the upstream end of the light transmitting tip for supporting a filter thereon, wherein said passage means for interconnecting the outer chamber with the inner chamber extends through a wall of said shield in a location between the filter supported on the annular surface and the upstream end of the light transmitting tip.

8. The irradiation device of claim 1 characterized in that housing includes opposed plastic sections that are separable from each other, said heat shield including a downstream metal threaded end for receiving a metal threaded upstream end of the light transmitting tip, said light transmitting tip including a surface for engaging a forwardly facing surface of a plastic housing section for pressing and maintaining the plastic housing sections in assembled relationship with each other.

9. The irradiation device of claim 8 characterized in that the heat shield includes metal sections threadedly connected to each other for enclosing the light-emitting lamp assembly and being separable by unthreading to provide access to the lamp assembly.

10. The irradiation device of claim 1 characterized in that the passage means for interconnecting the outer chamber with the inner chamber is located between the downstream end of the lamp assembly and the upstream end of the light transmitting tip.

11. A hand-held irradiation device for directing radiation onto a substance in a desired wavelength range for curing said substance, said device being characterized by an elongate housing having a rear end and a forward end; a light-emitting lamp assembly located within said housing; a light transmitting tip extending outwardly of the forward end of the housing and having a downstream end adapted to be positioned adjacent the substance to be irradiated and an upstream end for receiving radiation from the light-emitting lamp assembly; a heat shield surrounding said lamp assembly and bridging the space between said lamp assembly and the upstream end of said light transmitting tip, said shield being spaced inwardly from the outer wall of the elongate housing to define an outer chamber between the shield and housing and an inner chamber within the shield; an entrance conduit for receiving a pressurized cooling gas communicating through the rear end of the housing and being attachable to a source of pressurized gas; an exit conduit means also communicating through the rear end of the housing for directing the pressurized gas out of the housing after it has moved through the outer and inner chambers and channeling means for directing substantially all of the pressurized gas from the entrance conduit, through the outer and inner chambers in opposite directions, and out of the elongate housing through the exit conduit means.

12. The irradiation device of claim 11 characterized in that the housing includes inner and outer rear walls defining an annular space between them, said exit conduit means including circumferentially spaced-apart exit passages extending through the inner rear wall of said housing and said outer rear wall of said housing also having circumferentially spaced-apart openings through which ambient air is drawn by the movement of the pressurized gas through the exit passages in the inner rear wall.

13. The irradiation device of claim 12 characterized in that the circumferentially spaced-apart openings in the outer rear wall of the housing are out of radial alignment with the circumferentially spaced-apart exit passages through which pressurized gas is adapted to pass.

14. The irradiation device of claim 11 characterized by filter means located adjacent the upstream end of the light transmitting tip and within said shield, said channeling means directing pressurized gas over said filter means as said pressurized gas is circulated through the housing.

15. The irradiation device of claim 14 characterized in that said shield includes a rearwardly facing annular surface between the light-emitting lamp assembly and the upstream end of the light transmitting tip for supporting a filter thereon, wherein said passage means for interconnecting the outer chamber with the inner chamber extends through a wall of said shield in a location between the filter supported on the annular surface and the upstream end of the light transmitting tip.

* * * * *